United States Patent [19]

Balassa et al.

[11] Patent Number: 4,822,607

[45] Date of Patent: Apr. 18, 1989

[54] ANTI-TUMOR AGENT AND METHOD

[75] Inventors: Leslie L. Balassa, Blomming Grove; John F. Prudden, Upper Nyack, both of N.Y.

[73] Assignee: Lescarden Ltd., New York, N.Y.

[21] Appl. No.: 938,331

[22] Filed: Dec. 4, 1986

Related U.S. Application Data

[63] Continuation of Ser. No. 821,221, Jan. 21, 1986, abandoned, which is a continuation of Ser. No. 741,199, Jun. 4, 1985, abandoned, which is a continuation of Ser. No. 553,877, Nov. 21, 1983, abandoned, which is a continuation of Ser. No. 321,789, Nov. 16, 1981, abandoned, which is a continuation of Ser. No. 167,775, Jul. 14, 1980, abandoned, which is a continuation-in-part of Ser. No. 736,770, Oct. 29, 1976, Pat. No. 4,212,857.

[51] Int. Cl.$^4$ ...................... A61K 35/32; A61K 35/60
[52] U.S. Cl. ....................................................... 424/95
[58] Field of Search ........................................... 424/95

[56] References Cited

U.S. PATENT DOCUMENTS

| | | | |
|---|---|---|---|
| Re. 28,093 | 7/1974 | Balassa | 424/95 |
| 3,318,774 | 5/1967 | Dingwall et al. | 424/95 |
| 3,966,908 | 6/1976 | Balassa | 424/95 |

OTHER PUBLICATIONS

Merck Index, 8th Ed., Merck & Co. Inc., Rahway, N.J., 4968, pp. 137 and 138.

Carter et al., Chemotherapy of Cancer, 2nd Ed., Wiley & Sons, N.Y., N.Y., 1981, pp. 26–43.

*Primary Examiner*—Jerome D. Goldberg
*Attorney, Agent, or Firm*—Darby & Darby

[57] ABSTRACT

A method for treating carcinoma of the breast, carcinoma of the prostate, carcinoma of the colo-rectal area and carcinoma of the ovary having the properties of anaplasia, invasion and metastasis by administration of a granulated animal cartilage product or an aqueous extract thereof.

20 Claims, 3 Drawing Sheets

FIG. 1

FIG. 2

AREA IN SIZE RANGE (SQ. MICRONS)
PATIENT NO. 5 (MB)

FIG. 3

ANTI-TUMOR AGENT AND METHOD

This application is a continuation of application Ser. No. 06/821,221 filed Jan. 21, 1986, now abandoned, which was a continuation of application Ser. No. 06/741,199 filed June 4, 1985 now abandoned which was a continuation of Ser. No. 06/553,877 filed Nov. 21, 1983 now abandoned which was a continuation of application Ser. No. 321,789 filed Nov. 16, 1981 now abandoned which was a continuation of application Ser. No. 06/167,775 filed July 14, 1980 now abandoned which is a continuation-in-part of copending application Ser. No. 736,770 (now U.S. Pat. No. 4,212,857), filed Oct. 29, 1976.

This invention relates to a method of treating malignant human tissue tumors. More specifically, the invention relates to a method for suppressing and retarding the growth of carcinoma of the prostate, carcinoma of the colo-rectal area, carcinoma of the breast and carcinoma of the ovary by administration of a granulated animal cartilage product or an aqueous extract thereof.

In the past a variety of compounds have been experimentally investigated in an effort to find clinically effective anti-tumor agents. In general, this research has been specifically directed toward the discovery of compounds which can control, suppress, or retard the growth of malignant neoplasms. Malignant neoplasms are generally considered the new growth of tissue in which the growth is uncontrolled and progressive and is accompanied by a high degree of anaplasia. Malignant neoplasms also have the properties of invasion and metastasis.

Several chemotherapeutic agents have been found to be useful in treating malignant neoplasms (hereinafter referred to as tumors) in humans. Broadly classified, the chemotherapeutic agents found to be of assistance in the suppression of tumors include alkylating agents (e.g. nitrogen mustards), antimetabolites (e.g. pyrimidine analogs), radioactive isotopes e.g. phosphorus and iodine), hormones (e.g. estrogens and adrenocorticosteroids), miscellaneous agents (e.g. substituted ureas) and natural products (e.g. Vinca alkaloids and antibiotics). Although the preceding compounds are not curative agents, they are widely recognized in the medical profession as useful in the suppression, palliation, retardation and control of malignant tumors. While these compounds have been found to be effective and are in general clinical use as antiproliferative agents, there are well recognized drawbacks associated with their administration. The alkylating agents have marked cytotoxic action and the ability of these drugs to interfere with normal mitosis and cell division can be lethal. The antimetabolites can lead to anorexia, progressive weight loss, depression and coma. Prolonged administration of antimetabolites can result in serious changes in the bone marrow. Both the alkylating agents and antimetabolites generally have a depressive effect on the immunosupressive system. Prolonged administration of natural products such as Vinca alkaloids can also result in bone marrow depression. Hydroxyurea and other chemically derived agents can lead to a rapid reduction in the levels of adrenocorticosteroids and their metabolites. The administration of hormonal compounds or radioactive isotopes is also undesirable from the viewpoint of inflicting damage on the immunosupressive system and thereby disabling the body's defenses against common infections. In most instances it would be preferable to employ a chemotherapeutic agent which is effective in controlling, retarding or suppressing the growth of malignant tumors while simultaneously acting to stimulate the patients immune system. Preferably, such a medicament should also have a low level of toxicity with respect to nonafflicted organ tissues.

It has now been unexpectedly discovered that a composition consisting of finely divided cartilage tissue derived from animals, reptiles and fish can be used as an effective palliative agent to control, suppress and retard the growth of carcinoma of the prostate, carcinoma of the colo-rectal area, carcinoma of the breast, and carcinoma of the ovary. The palliative anti-tumor action provided by the administration of processed animal cartilage materials has also been found to stimulate the immune system of the afflicted individual and to result in enhanced levels of immunoglobulins and complement.

Accordingly, one aspect of the present invention is to provide a method of suppressing the growth of carcinoma of the prostate, carcinoma of the colo-rectal area, carcinoma of the breast, and carcinoma of the ovary in human tissue by administering a finely divided animal cartilage product.

Another aspect of this invention involves a method of suppressing the growth of the above-mentioned human tissue tumors by administration of an aqueous extract of granulated animal cartilage.

A further aspect of the present invention is to provide a method of retarding and suppressing the growth of the above-mentioned malignant tumors in human tissue while simultaneously stimulating the immune system of the afflicted individual by administering an effective quantity for tumor suppression and immune system stimulation of processed animal cartilage.

A still further aspect of the present invention is the provision of an oral dosage form of anti-tumor agent effective against the above-mentioned tumors.

As used in the present specification the term "cartilage extract" refers to an aqueous extract derived from granulated animal fish or reptile cartilage.

U.S. Pat. No. Re. 28,093 describes the preparation and use of cartilage powder to accelerate and improve the healing of certain types of wounds. U.S. Pat. No. 3,966,908 discloses that aqueous extracts derived from granulated animal cartilage are useful in the treatment of degenerative joint diseases in mammals. Both of the preceding patents, the disclosures of which are incorporated herein by reference, teach the preparation of cartilage powder and aqueous cartilage extracts.

The cartilage employed to prepare the active material of the present invention is preferably derived from young cartilage, i.e. cartilage from young animals, or young or newly regenerated cartilage from older animals such as reptiles or from species such as fish or shark in which cartilage remains "young" for the life of the animal. Where age is the criteria for defining "young" the cartilage is preferably derived from animals less than 6 months old. It has been found that cartilage derived from older animals is also useful in preparing the anti-tumor agents effective against carcinoma of the prostate, carcinoma of the colo-rectal area, carcinoma of the breast, and carcinoma of the ovary of the present invention, but that such extracts are somewhat less effective.

The present invention provides a dosage unit of an effective amount for retarding tumor growth of the above-mentioned tumors of essentially pure, defatted cartilage either in finely divided powder form or in the form of an aqueous cartilage extract.

The cartilage powder employed as the oral dosage unit of the present inventor is obtained from the cartilage of a young animal, a mature animal, or fish or a reptile and can have a particle size between about 1 and 500 microns. Preferably the cartilage has an average particle size between about 40 micron and 100 microns and a substantial maximum particle size of about 500 microns. Suitable cartilage powder for incorporation in the oral dosage forms of the present invention may be prepared according to the methods described in U.S. Pat. No. 3,400,199 (U.S. Pat. No. Re. 28,093) and U.S. Pat. No. 3,966,908. However, in contrast to the teaching of these patents, for use as an anti-tumor agent effective against the four types of carcinomas mentioned above in the present invention the powder may have a maximum particle size of up to about 500 microns.

The raw cartilage may be prepared by any suitable means as taught in the above referenced patents to result in a product which is essentially pure cartilage substantially free from adhering tissue which may have been removed by acid pepsin digestion or other suitable treatment, with or without mechanical assistance or otherwise.

An anti-tumor agent useful for parenteral administration to patients afflicted with the specific carcinomas mentioned above may be prepared by making an aqueous extract of the finely divided cartilage material. The average size of each finely divided cartilage particle is not critical and successul extracts have been prepared using particles as large as 5 centimeters or more, although it has been found that more efficient extraction can be conducted when the cartilage is first pulverized to a particle size below about 500 microns. Pulverization of the cartilage material may be accomplished using any number of techniques including ball milling, hammer milling in an inert atmosphere, pebble milling and fluid energy mill grinding.

The granulated cartilage material may be extracted according to the methods described in U.S. Pat. No. 3,400,199 (U.S. Pat. No. Re. 28,093).

In general, cartilage extracts are obtained through the use of pharmaceutically acceptable aqueous extracting agents which dissolve the active component of the granulated animal cartilage. Thus, the extract is a product from which a substantial portion of the nonactive components have been removed and therefore has a higher concentration of activity per unit dose. Examples of suitable extraction aids include ammonia or ammonium carbonate, or such materials which on remaining in the extract would be pharmaceutically acceptable. Examples of other extraction aids include urea, sodium citrate, disodium phosphate, trisodium phosphate, sodium formate, sodium chloride, and similar compounds or mixtures of them. The extract may be dialyzed to remove undesired salts or other dialysable material which may be present. In one embodiment of the invention the cartilage extract may be dialysed to separate impurities thereby yielding a product which provides enhanced activity in some circumstances.

The cartilage extract preferably used, in the present invention is an injectable dosage form of granulated bovine tracheal cartilage extracted with isotonic saline solution. In one preferred embodiment of the invention, the isotonic saline extract is made into an injectable dosage form by dilution with sterile water to yield a sterile solution. The liquid used to extract cartilage powder for preparation of an injectable dosage unit is usually isotonic saline solution containing 0.9% NaCl (USP injectable saline), however the invention is not limited to using this material as the injectable extraction liquid. The aqueous cartilage extract may be suspended in oils such as soybean oil, corn oil, olive oil or linseed oil. The oil dispersions may be emulsified in water, forming oil in water type emulsions, or conversely, water may be emulsified in the oil dispersions forming water in oil emulsions.

The injectable cartilage extracts of the present invention contain from about 1 to about 10% and preferably about 6% cartilage extract diluted in sterile water, USP injectable saline or the like. In most instances, the sterile extract to be used for injection contains a preservative such as benzyl alcohol, or paraben and is a light brown translucent liquid that is slightly viscous at 20° C. and a gel at 0° C. The extract may be prepared by heating the aqueous cartilage suspension for about at least approximately 15 minutes up to 24 hours or more at temperatures from about 75° C. to about 130° C., or preferably by autoclaving for 90 minutes at 15 lbs. pressure at 121° C. with all adjuvants, if any be employed. Immediately prior to administration, the injectable dosage solution can be diluted approximately 10% with 1% lidocaine (or equivalent local anesthetic) to alleviate possible discomfort. However this is usually not required due to the anesthetic effect of the benzyl alcohol employed as a preservative.

In use as an anti-tumor agent for treating the above-mentioned carcinomas, the sterile cartilage extract is preferably administered subcutaneously in those areas of the body possessing a readily distensible subcutaneous space (e.g., the back, anterior thorax, abdomen and anterior thighs). The extract need not be introduced directly at the site or adjacent to the location of the malignant growth although it has been observed that tumor retardation and suppression is enhanced when the cartilage extract is injected into the area directly adjacent to the lesion.

Administration is carried out by injecting (either parenterally or subcutaneously) from about 1 to 75 cc. and preferably from about 25 cc to about 50 cc of the sterile cartilage extract into each of several subcutaneous sites or depots. Preferably, a total of between about 25 and 200 ccs. of cartilage extract is administered during each treatment, although smaller quantities on the order of from about 1 to about 50 cc can be administered at more frequent intervals in the interest of patient comfort. Similarly larger amounts up to 800 cc can be administered (under brief general anesthesia) in multiple depots at less frequent intervals. In view of the relatively large volumes of medication which are to be injected, the speed of injection is intentionally slow to minimize discomfort.

Each depot should contain not less than about 1 cc nor more than about 75 cc of the sterile cartilage extract. In most cases a subcutaneous depot containing about 50 cc of the sterile extract has been found to provide good results.

To minimize any discomfort attributable to the relatively large volume of the subcutaneous depots in some sensitive patients, the injectable solution may desireably contain up to about 10% by weight of lidocaine or a similar material having localized anesthetic action. Between about 4 and about 48 hours is usually required for the aqueous cartilage extract located in each depot to be absorbed into the tissues of the body and eventually into the bloodstream thereby dissipating the cartilage depot.

The cartilage powder of the invention is administered via the oral route. In the preparation and administration of oral dosages a variety of solid pharmaceutical formulations may be employed, such as capsules or tablets. The quantity of effective dose supplied by each capsule or tablet is relatively unimportant as the total oral dosage can be achieved by administration of either one or a plurality of capsules or tablets, or both. Preferably hard shell capsules are employed as the oral dosage form and may comprise any well known pharmaceutically acceptable capsule material e.g. gelatin or cellulose derivatives. The tablet dosage form of the invention may be prepared using conventional tabletting procedures and may include solid carriers, lubricants and other well known tabletting ingredients. Starch, sugar and bentonite exemplify the solid carriers that may be used in tabletting the cartilage powder of the invention. The capsules and tablets of the invention may contain between about 50 and 1000 milligrams and preferably between about 250 and 500 milligrams of the active cartilage powder ingredient. An especially preferred oral dosage form comprises a hard gelatin capsule containing 375 milligrams of finely divided cartilage powder having an average particle size of between 40-100 microns.

The oral dosage forms are administered at a dosage level of between about 3,000 and 12,000 milligrams per day. A dosage level of 9,000 milligrams per day has been found especially effective in several clinical instances. The daily dose is generally subdivided into 3 separate doses of between about 1,000 and 4,000 milligrams, and preferably 3,000 milligrams which may be ingested at four to six hour intervals during the day. At the preferred 9,000 milligram per day rate each dose is preferably administered in the form of a plurality of hard shell gelatin capsules containing 375 milligrams of active ingredient.

The effective dosage, frequency of administration, and duration of treatment of the medicaments of this invention depends upon the severity of condition, the stage, and individual characteristics of each host being treated. Clinical evaluations of the present invention reveal that many subjects suffering from one of the four carcinomas mentioned above display objective evidence of tumor regression and enhanced titers of immunoglobulins after receiving between 50 to about 400 cc per week of the aqueous cartilage extract of the present invention (or between 6,000 and 12,000 mgs. per day of oral cartilage powder) for a period of at least about four to eight weeks.

Further observations confirm that the cartilage products of the present invention provide an effective anti-tumor action on confirmed malignant tumors including those of the intestinal ovary, prostate, breast, and colorectal area. The length of clinical remission achieved on administration of the present invention varies from patient to patient depending upon the severity and extent of the disease, tumor volume and location and the patients general physical condition. In several instances patients have remained in complete remission for a period of several months to three years or more. In a majority of those cases where tumors recurred, the administration of a maintenance dose equivalent to an average daily dosage (i.e. injection of between about 50 and 100 cc of cartilage extract into two to four subcutaneous depots at one time (twice weekly) or ingestion of 6,000 to 9,000 mg. per day of cartilage powder) resulted in re-establishing tumor regression and suppression.

The degree of remission achieved by patients treated in accordance with the present invention was objectively measured by various means including biopsy, surgical excision, direct observation (e.g. gastro-esophagoscopy X-ray, fluoroscopy, cystoscopy), palpation, and laboratory hematological tests. Tumor regression was also confirmed by palpation and direct measurement of the volume or mass of those growths when anatomical location made it possible to carry out such evaluations on a regular basis.

Objective measurements made with an optical scanning microscope also confirmed that a fundamental change had occurred in the cellular structure of the specific malignant growth.

This microscopic evaluation was carried out by scanning paraffin-embedded tissue biopsy sections obtained from patients at various stages of treatment with the present invention using an optical scanning microscope linked to an image analyzing computer. This apparatus is available from Imanco, Ltd. Cambridge, England, as the Quantimet 720. The device incorporates a high resolution television camera (scanning 720 lines at a rate of 10 frames per second). The camera is programmed to integrate gray levels from the viewing surface with cellular morphology (e.g., optical density of nucleus and optical density of cytoplasm) as well as perimeter size of nucleus and cytoplasm sections, through a microscope and to derive an analog signal from this information. The analog signal is converted to a digital value based on gray levels in the black and white image. In the present instance, the computerized image scanning apparatus was programmed to derive an analog signal based upon nuclear area and morphology and to determine the total number of features (i.e. nuclei) within the scanning area that fell within particular nuclear size ranges. Thus, it was possible to obtain an analysis of each tissue biopsy which gave the total number of cells counted, the area size range in square microns of each cell's nucleus, and the total number of cell nuclei in each size range as a percentage of the total number of cells observed by the camera. Utilizing this information it was possible to derive a mean nuclear area for each tissue biopsy. Since it is well recognized that malignant cells generally possess larger nuclei, it was possible to determine the effect of the cartilage agents of the present invention upon size of the nuclei. The results of the analysis are discussed in conjunction with the graphs presented as FIGS. 1-3.

Analysis of various blood fractions associated with the immune system indicates that administration of cartilage products according to the present invention apparently stimulates the B cells of this system and produce increased titers of various antibodies and immunoglobulins. Patients undergoing treatment with the present invention show sharply increasing levels of immunoglobulins A and M, as well as increasing titers of total complement and C3 complement. However, no effect has been discerned on T cells or macrophages. While not wishing to be bound to any particular theory of operation for the immune stimulating aspect of the present invention, we believe that its mechanism of action may be to elicit the production of antibodies which are more effective in dealing with the "foreign" antigens which have already been detected in certain cancers. The following examples illustrate the preparation of cartilage products which are useful as anti-tumor agents for treating carcinoma of the prostate, carcinoma of the colo-rectal area, carcinoma of the breast and carcinoma of the ovary according to the present invention.

EXAMPLE I

Cartilage Pebble Mill-Ground

The tracheas of healthy adult beef cattle were removed within 30 to 60 minutes after the animals were slaughtered. The tracheas were then either processed immediately with an acid-pepsin solution or they were frozen to preserve them, in which case the acid-pepsin digestion may be deferred. The tracheas, either fresh or previously frozen, were then digested for about six hours at 50° C. in an aqueous solution containing 0.6% acetic acid (U.S.P. glacial) and 0.3% pepsin (N.F. IX grade, 3500 activity). After digestion the tracheal cartilage was removed from the acid-pepsin solution, washed first with water of about 70° C. and then with water of about 25° C. until the effluent wash water showed no trace of pepsin or acetic acid. The cartilage was dried in vacuum (20 mm mercury) at 80° C. The dried cartilage was defatted by extracting it with a solvent, such as hexane. It was then granulated in a sealed ball mill under an inert atmosphere and the ground material strained through a 100 mesh strainer. The resulting cartilage granules ranged in size from about 50 to about 500 microns.

EXAMPLE II

Cartilage obtained from the tracheas of a one month old calf was obtained by the same procedure as described in Example I and the resulting cartilage was ground to an average particle size of about 500 microns in a laboratory four-quart size porcelain jar mill loaded with one inch size (average) flint pebbles in a weight ratio of 1 cartilage to 2 pebbles. Dry ice ($CO_2$) was then put on top of the mill charge. The lid of the mill was then clamped on tight and the mill rotated as is customary in the performance of a grinding operation. The grinding was carried out at about 20° C. for 96 hours. Resulting cartilage granules (approx. 40–200 microns) were thoroughly admixed in aqueous; isotonic saline, and the admixture heated in an autoclave at 121° C. for about 90 minutes at 15 pounds pressure to complete the extraction. The suspended matter was removed by centrifugation and the resulting tan liquid used to fill 50 ml. vials, and then sterilized in the autoclave at 121° C. for 15 minutes at 15 psi. Cartilage powder may also be obtained from cartilage sources such as pigs, lambs, goats, skeleton of sharks, rodents, crocodiles, birds, fish, etc. Reptile cartilage is particularly desirable in view of the ability of reptiles to regenerate their tissues and even their limbs. More details on preparing cartilage powder from these and other sources will be found in U.S. Pat. No. Re. 28,093.

EXAMPLE III

Liquid cartilage extracts were prepared as follows:
The cartilage obtained from a one day old calf was acid-pepsin digested as in Example I, granulated to an average particle size of about 0.2 cm, and then without drying was suspended in the extracting liquid, isotonic saline solution, and then transferred into a pebble mill which was charged to 50% of its volume with flint pebbles of average size, one inch diameter. The ratio of the cartilage to extracting liquid was kept to 25:75. The liquid suspension was charged into the mill in a quantity just sufficient to fill the voids of the pebbles with the top of the pebbles barely covered by the liquid. The air was then purged from the mill with nitrogen and the mill closed. The mill was allowed to run for 6 hours at between 3° C. and 4° C., which resulted in a medium fine grinding of the cartilage granules and in the simultaneous extraction of the active tumor suppressive agent effective against the four carcinomas mentioned above from the cartilage.

At the end of the 6-hour cycle, the mill was emptied, the fluid paste strained free of the pebbles, the fluid transferred into a centrifuge operated at 6000 r.p.m. and at a temperature of between 3° C. After one-half hour the centrifuge was stopped and the supernatant liquid strained through a 400 mesh nylon screen. If the strained extract was cloudy, it was returned to the centrifuge and the centrifuging repeated until a clear slightly opalescent extract was obtained.

The extracts were stored at 40° C. preserved with 0.9% benzyl alcohol.

The following extracts were prepared according to the present invention:

| | Cartilage Source | Extracting Liquid | Total Solids of Clear Extract, By Weight, Percent |
|---|---|---|---|
| a | Bovine trachea | Distilled water | 1.3 |
| b | Bovine trachea | Isotonic saline sol. | 5.2 |
| c | Bovine trachea | Ammonia (28%) 1% in water | 6.5 |
| d | Bovine trachea | 2% urea in water | 9.6 |
| e | Bovine trachea | 1% ammonium carbonate in water | 6.4 |
| f | Bovine trachea | 1% disodium phosphate in water | 6.6 |
| g | Bovine trachea | 3% ammonium carbonate in water | 7.2 |
| h | Bovine trachea | 1% trisodium phosphate in water | 7.6 |
| i | Bovine trachea | 1% sodium citrate in water | 7.0 |
| j | Bovine trachea | 3% sodium citrate in water | 9.2 |
| k | Bovine trachea | 1% sodium formate in water | 8.2 |
| l | Piglet 1 day old | Isotonic saline solution | 6.4 |
| m | Piglet 1 day old | 1% ammonia (28%) in water | 7.1 |
| n | Piglet 1 day old | 3% ammonium carbonate in water | 8.1 |
| o | Piglet 1 day old | 3% sodium citrate in water | 10.0 |
| p | Calf 1 day old | Isotonic saline solution | 6.2 |
| q | Calf 1 day old | 1% ammonia (28%) in water | 7.3 |

Note:
The isotonic saline solution was prepared with distilled water and contained 0.9% NaCl.

EXAMPLE IV 500 hard gelatin capsules available from Eli Lilly & Company (Indianapolis, Ind.) were filled with 375 mg. of the cartilage powder of Example I and stored at ambient temperature.

In addition to pebble mill and fluid energy mill grinding, satisfactory cartilage powders may also be obtained by ball milling, or hammer milling in air or preferably under an inert gas atmosphere.

While ball or pebble milling the cartilage with the extracting liquid gives satisfactory results, other methods, such as mixing the cartilage powders in the liquids with a high speed, high shear, closed turbine mixer or passing the extraction mixture through a pressure homogenizer, preferably at pressures in excess of 4000 p.s.i. will also give extracts of high activity.

A group of 15 patients afflicted with malignant tissue tumors (i.e. individuals with pathologically confirmed malignant tumors) including carcinoma of the breast, carcinoma of the prostate, carcinoma of the ovary and carcinoma of the colo-rectal area were treated in a continuing clinical situation by parenteral administration of aqueous cartilage extracts prepared according to Example II of the present invention, or with orally administered cartilage powder in capsule as prepared in Example IV.

In general, the parenteral treatment involved administration of between 50 to 400 cc of aqueous cartilage extract each week. In order to obtain controlled results each individual was treated by subcutaneously injecting a sterile solution containing 6% cartilage solids in the form of a saline cartilage extract (pH 5.5) into from 2 to 4 spaced apart (anatomically separated) depots. Each depot contained from about 25 to about 50 cc of the aqueous extract. After the initial stages of treatment, the dosage delivered at each administration and the frequency of administration was varied depending upon the individual's response to the drug as determined by retardation or suppression of tumor growth, immunoglobulin and complement assays, and the patient's general physical condition.

The patients on the oral regime received from 3000–9000 mgs. per day of cartilage powder in gelatin capsules as prepared in Example IV.

The following tabulation of case studies reports on the results obtained with cartilage therapy.

TABLE IV

| PATIENT IDENT., AGE & SEX | DIAGNOSIS | THERAPY | RESULTS |
|---|---|---|---|
| AF Age 62 Male #1 | Adeno Carcinoma Tumor-Stomach Wall Confirmed by gastroesophagoscopy & biopsy | 100 cc aqueous cartilage extract per week administered subcutaneously for 12 months (thighs and abdomen) | Gastro-esphagoscopy and biopsy show no evidence of neoplastic activity at the tumor site |
| CP Age 58 Female #2 | Recurrence of breast cancer in supraclavicular nodes 25 months after radical mastectomy- biopsy confirmed anaplastic form of breast cancer matching that of original tumor | 100 cc aqueous cartilage extract administered subcutaneously in thighs, abdomen or supraclavicular space each week for 12 months. | No evidence of supraclavicular nodes |
| FK Age 66 Female #3 | Large (Approx 20 mm) cancerous nodes in the right supraclavicular space confirmed by operative Biopsy | 50 cc Aqueous cartilage extract administered subcutaneously each week for 4 months, then 100 cc subcutaneously each week for 8 mos. | Surgical dissection of afflicted area for unrelated cause confirmed absence of neoplastic lesions Seven months after treatment ceased neoplastic lesion reappeared in right breast and right axilla- Cured by modified radical mastectomy. Remains well. |
| GDA Age 56 Male #4 | Tumor filling entire rectum-biopsy confirmed diagnosis of adeno carcinoma | 50 cc of aqueous cartilage extract administered subcutaneously each week for 8 weeks, then dosage increased to 100 cc subcutaneously per week for 16 months (Patient was sigmoidscoped and the lesions biopsied at 8 week intervals during treatment) Biopsy slides were evaluated using the Quantiment 720 computer assisted scanning microscope | Over period of 18 months original malignant mass (Approximately 30 centimeters) shrank to two benign polypys of 5 centimeters and 9 centimeters respectively which were removed trans-sigmoidscopically by snare-and-cautery with a wire loop. Patient continued on booster dose of 100 cc every 6th week. |
| MB Age 42 Female #5 | Metastastizing melanosarcoma characterized by large tumor masses on the left breast, medial to the right breast on the 8th, | 100 cc of aqueous cartilage extract administered subcutaneously every other day for a total of 850 cc. | Over an 18-day hospitalization period, 75% reduction in size of palpable tumor masses and reduced abdominal distention |

TABLE IV-continued

| PATIENT IDENT., AGE & SEX | DIAGNOSIS | THERAPY | RESULTS |
|---|---|---|---|
| | rib, on the scalp and in the left lobe of the liver and spleen. | | as the hepatic and splenic masses receded (Patient expired due to unrelated cause) |
| MK #6 | Colonic tumor confirmed by barium enema and colonoscopic biopsy | Administration of 100 cc of aqueous cartilage extract into two 50 cc depots subcutaneously once a week for one year | Barium enemas confirmed decrease in size of the ulcerating tumor |
| MM Age 74 Male #7 | Squamous cell carcinoma in the left upper lobe bronchus confirmed by cytologic study | Administratioin of 100 cc of aqueous cartilage extract subcutaneously per week for 17 months | Cytologic studies declined from Clas IV ("Malignant") to Class II ("Not normal-no definite malignancy identified-more study advised"). Chest films interpreted as negative. |
| MS Age 72 Female #8 | 57 of 61 nodes positive (including several apical nodes following radical mastectomy. Histiology of the excised lesion was extremely anaplastic | Dosage of 100 cc of cartilage extract subcutaneously per week in two 50 cc adjacent depots directly to the afflicted areas including administration in the supraclavicular area, over the right anterior chest wall, and over the right deltoid-treatment continued for 2½ years (total treatment time 4½ years) | Supraclavicular mass progressively shrank as did all recurrent nodules over the chest wall and on the dorsal aspect of the right arm. |
| PS #9 | Extensive angiocarcinoma lesions on the trunk, arms, and legs | 100 cc of aqueous extract administered weekly into 50 cc subcutaneous depots closet to locations where high density lesions were apparent (total dose is 14,000 cc as of 9/1/76) | Lesions have progressively decreased in size on the trunk, arms and legs |
| ZH Age 77 Female #10 | Ulcerated tumor fixed to the chest wall and palpable nodes on the right supraclavicular space confirmed by biopsy | 100 cc of aqueous cartilage extract administered weekly via the subcutaneous route in from 2 to 4 depots in the arms, thighs, and thorax. | Supraclavicular space virtually normal after approximately 7 months treatment - Few thin scars represent healed malignant ulcer |
| LA Age 76 Male #11 | Prostate carcinoma | 4500 mgs. oral cartilage powder per day for 1 year; dose increased to 9000 mgs. per day. Total dose 8130 gm; duration of treatment 25 mos. | Remission |
| HG Age 61 Male #12 | Prostate carcinoma | 4500 mgs. oral cartilage powder per day for 6 mos. then 6000 mgs. per day for 11 mos. total dose 3035 gms. | Remission |
| RG | Carcinoma of | 4500 mgs. oral | Remission |

TABLE IV-continued

| PATIENT IDENT., AGE & SEX | DIAGNOSIS | THERAPY | RESULTS |
|---|---|---|---|
| Age 63<br>Male<br>#13<br>Male | prostate confirmed by trans urethral resection | cartilage powder per day; total dose 4280 gm. | |
| DF<br>Age 37<br>Male<br>#14 | Embryonal cell carcinoma of left testicle (diagnosed at radical orchidectomy) | 3000 mgs. oral cartilage powder per day for 2 weeks then 4500 mgs. per day total dose 8946 gms. | Symptomatic remission normal HCG |
| Cr<br>Age 83<br>Male<br>#15 | Large multifocal radiation resistant basal cell carcinoma of the skin of the back. | 6000 mgs. oral cartilage per day, then 3000 mgs. per day total dose 3360 gms. | Remission confirmed by biopsy |
| EC<br>Age 60<br>Female<br>#16 | Carcinoma of stomach confirmed at gastrectomy | 9000 gms. oral cartilage powder per day | Remission confirmed by G-I series; no delay in barium transit. |

In none of the preceding cases were there any instances of toxicity or abnormal liver chemistry, disturbed renal function or evidence of sensitivity attributable to the cartilage agents of the invention. Immunoglobulin and complement assays on several patients revealed increasing titers of mmunoglobulins A, and M, C3 complement, and total complement.

Conventional mitogenesis assays were performed on patients receiving oral cartilage anti-tumor therapy according to the present invention. The assays used the general mitogens Phytohemagglutinin (PHA) and Concanavalin A (Con-A) both of which are T-cell mitogens and Pokeweed mitogen (PWM) which is a T-cell dependent B-cell mitogen. Analysis of the assays confirms that the cartilage products of the present invention have high stimulation indices (SI).

| Patient # | Cartilage Powder Dose Hard Shell Capsules | Stimulation Indices Utilizing | | |
|---|---|---|---|---|
| | | PHA | CON-A | PWM |
| 1 | 9 Gms Per Day | P 48.1<br>NVS 19.9 | P 65.1<br>NVS 43.1 | P 68.0<br>NVS 28.2 |
| 2 | 9 Gms Per Day | P 15.9<br>NVS 38.8 | P 30.14<br>NVS 14.9 | P 57.8<br>NVS 54.0 |
| 3 | 9 Gms Per Day | P 142.0<br>NVS 72.0 | P 96.0<br>NVS 36.0 | P 275.0<br>NVS 127.0 |
| 4 | 9 Gms Per Day | P 1,569.0<br>NVS 40.0 | P 290.0<br>NVS 105.0 | P 257.0<br>NVS 158.0 |
| 5 | 9 Gms Per Day | P 663.0<br>NVS 105.0 | P 532.0<br>NVS 22.0 | P 453.0<br>NVS 79.0 |
| 6 | 9 Gms Per Day | P 35.0<br>NVS 46.0 | P 120.0<br>NVS 43.0 | P 148.0<br>NVS 73.0 |

P = SI value for patients receiving oral cartilage powder treatment.
NVS = Average SI value obtained from 3 normal volunteers (not receiving any cartilage treatment).

The variation in the stimulation indices of the normal volunteer subjects is due to differences in the time of assay following venipuncture, laboratory conditions at the time of assay, etc. This variation does not affect the direction or magnitude of the increase in the stimulation index in any one test since the patient and the normal volunteers to whom he is compared are always tested simultaneously.

Since lymphocyte activation, as measured by the stimulation index in these results, is generally regarded as the mechanism by which the immune system eliminates or inhibits malignancy, these results are consistent and confirmatory of the anti-tumor activity of the cartilage products of the present invention against the four carcinomas mentioned above.

Slides of tissue tumors obtained at varying intervals from patients 4, 5 and 8 (in Table IV) were scanned with the Quantimet 720 apparatus and integrated to digital values by the computer. The results of the analysis are presented graphically in FIGS. 1-3.

GDA—PATIENT NO. 4 FROM TABLE IV

Slide #A of patient GDA (No. 4) was obtained from a biopsy taken about 20 weeks prior to the commencement of treatment. The mean nuclear size (area) of the cells observed was 32.5 microns. (No graph shown).

Slide #1 (FIG. 1) of patient GDA was obtained by a biopsy taken on the day before treatment commenced. It can be seen that the mean nucleus size remained the same as in slide A (approx. 32.5 microns).

GDA slide #2 (FIG. 1) was obtained from a biopsy taken approximately 8 weeks after treatment commenced. The mean size of the nuclei had decreased to 27.5 microns. This is a decrease of 16% over the mean nuclear size prior to the commencement of treatment.

PATIENT NO. 5—MB FROM TABLE IV

Slide #1 (FIG. 2) of patient No. 5 was obtained from a biopsy taken several days prior to the commencement of treatment. As determined from the computer printout obtained from the Quantimet apparatus, the mean nuclear size was 62.5 microns. In addition, a large number of nuclei having areas greater than 80 microns were observed.

Slide #2 (FIG. 2) was obtained from a biopsy taken 18 days after the commencement of treatment. The mean nuclear size decreased to 33.0 microns, a decrease of 47%. Very few cells were observed in which the nuclei had an area greater than 75 microns.

PATIENT NO. 8—MS—FROM TABLE IV

MS slide #1 (FIG. 3) was obtained prior to starting administration of 100 ccs. of cartilage extract per week. The mean size of the cell nuclei was approximately 55 microns.

MS slide #2 (FIG. 3) was obtained from a biopsy taken about 10 months after slide #1. During this period the patient had been receiving 100 ccs. of aqueous cartilage extract subcutaneously each week in two 50 cc depots. The mean nuclear size on slide #2 declined to 25.0 microns, a decrease of 55%. In addition, the nuclei size distribution shifted downward (indicating a sharp decrease in the number of malignant cells being observed).

Figure 1:
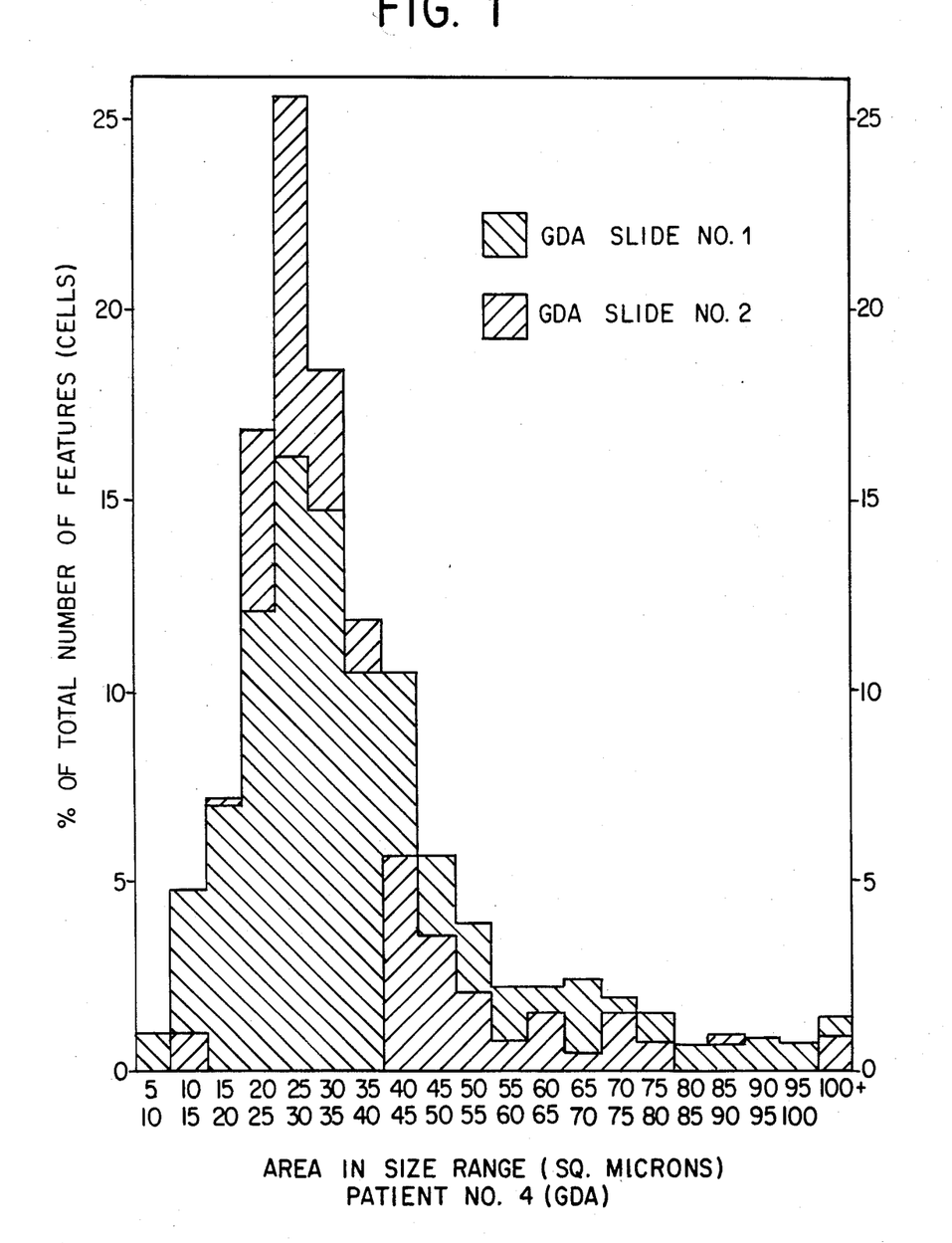
Figure 2:
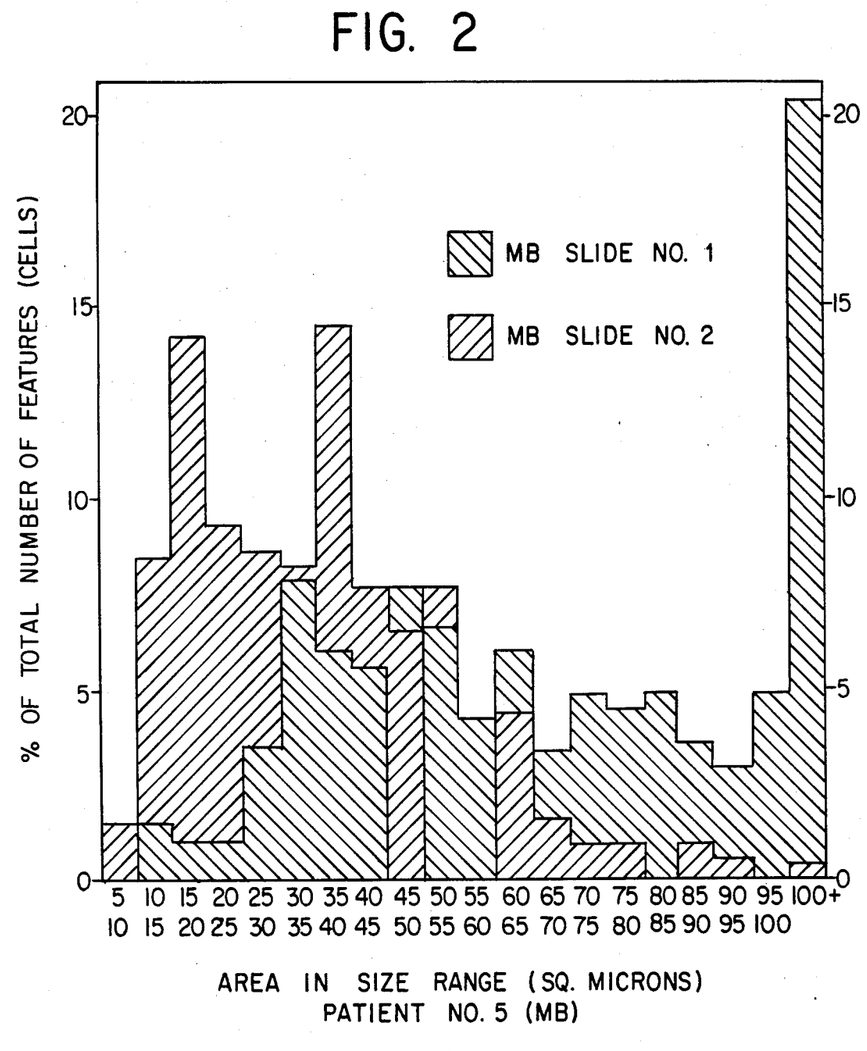
Figure 3:
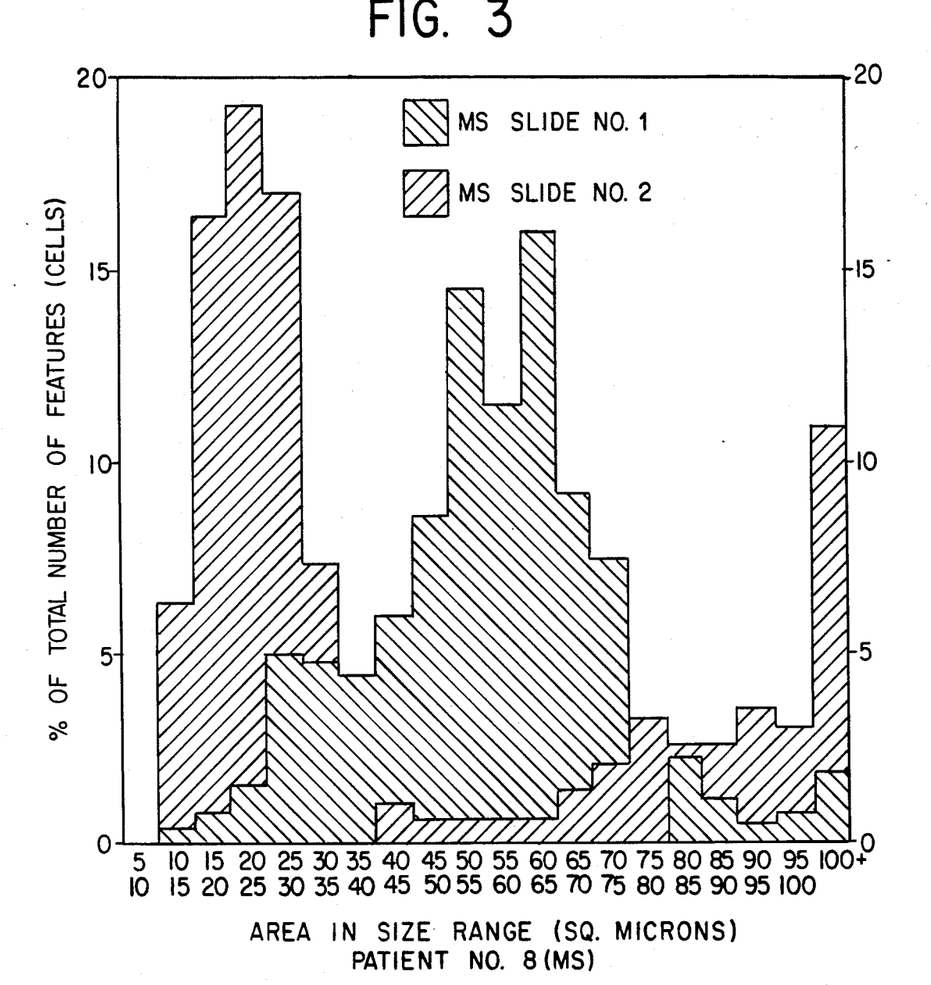

The results of the Quantimet image analyzing computer analysis indicate that administration of the cartilage product of the present invention had a direct effect on the mean nuclear size of cells biopsied from afflicted tumor tissues.

All of the foregoing image scanning analyses confirm that administration of cartilage according to the present invention leads to a decrease in the nuclear area of the specific confirmed malignant cells. Such a decrease is generally interpreted as a sign that the cells in which the nuclei reside are returning to more stable mitotic patterns of the type associated with normal non-malignant cell replications.

Salts other than NaCl may provide more effective extraction, as shown in Example II. An inert atmosphere during the extraction results in extracts of greater potency than when the extraction is carried out in the presence of oxygen. However, since the presence of oxygen during processing has in some instances completely inactivated extracts of the cartilages herein shown otherwise to be vastly superior, the use of well-known, pharmaceutically acceptable non-toxic antioxidants such as ascorbic acid or its salts, or vitamin A may permit carrying out the extraction in the presence of air without serious loss of potency.

What is claimed is:

1. A method of treating conditions selected from the group consisting of carcinomas of the breast, ovary, prostate gland, and colo-rectal area, which comprises subcutaneously administering in a distensible area of the body to a patient afflicted with said carcinoma an effective amount for treating said carcinoma of an aqueous solution consisting essentially of the aqueous soluble portion of essentially pure granulated cartilage materials substantially free from adhering tissue, said cartilage being derived from a cartilage bearing animal, fish or reptile.

2. The method of claim 1 wherein said effective amount comprises from about 1 cc to about 400 cc of said cartilage extract per week.

3. A method of treating ovarian carcinoma which comprises subcutaneously administering in a distensible area of the body to a patient afflicted with said carcinoma an effective amount for treating said carcinoma of an aqueous solution consisting essentially of the aqueous soluble portion of essentially pure granulated cartilage materials substantially free from adhering tissue, said cartilage being derived from a cartilage bearing animal, fish or reptile.

4. The method of claim 3 wherein said effective amount comprises from about 1 cc to about 400 cc of said cartilage extract per week.

5. A method of treating carcinoma of the prostate gland which comprises subcutaneously administering in a distensible area of the body to a patient afflicted with said carcinoma an effective amount for treating said carcinoma of an aqueous solution consisting essentially of the aqueous soluble portion of essentially pure granulated cartilage material substantially free from adhering tissue, said cartilage being derived from a cartilage bearing animal, fish or reptile.

6. The method of claim 5 wherein said effective amount comprises from about 1 cc to about 400 cc of said cartilage extract per week.

7. A method of treating carcinoma of the colo-rectal area which comprises subcutaneously administering in a distensible area of the body to a patient afflicted with said carcinoma an effective amount for treating said carcinoma of an aqueous solution consisting essentially of the aqueous soluble portion of essentially pure granulated cartilage material substantially free from adhering tissue, said cartilage being derived from a cartilage bearing animal, fish or reptile.

8. The method of claim 7, wherein said effective amount comprises from about 1 cc to about 400 cc of said cartilage extract per week.

9. The method of treating a malignant carcinoma of the breast which comprises orally administering to a patient afflicted with said carcinoma of the breast a solid dosage form containing an effective amount for treating said carcinoma of finely divided cartilage powder having a particle size between about 1 micron and about 500 microns, said cartilage powder being derived from a cartilage bearing animal, fish or reptile and consisting essentially of defatted and essentially pure granulated cartilage material substantially free from adhering tissue.

10. The method of claim 9 wherein said effective amount comprises between about 3 and about 12 grams of said cartilage powder per day.

11. The method of treating a malignant carcinoma of the prostate gland which comprises orally administering to a patient afflicted with said prostate carcinoma a solid dosage form containing an effective amount for treating said prostate carcinoma of finely divided cartilage powder having a particle size between about 1 micron and about 500 microns, said cartilage powder being derived from a cartilage bearing animal, fish or reptile and consisting essentially of defatted and essentially pure granulated cartilage material substantially free from adhering tissue.

12. The method of claim 11 wherein said effective amount comprises between about 3 and about 12 grams of said cartilage powder per day.

13. A method of treating a malignant carcinoma of the ovary which comprises orally administering to a patient afflicted with said ovarian carcinoma a solid dosage form containing an effective amount for treating said carcinoma of finely divided cartilage powder having a particular size between about 1 micron and about 500 microns, said cartilage powder being derived from a cartilage bearing animal, fish or reptile, and consisting essentially of defatted and essentially pure granulated cartilage material substantially free from adhering tissue.

14. The method of claim 13 wherein said effective amount comprises between about 3 and about 12 grams of said cartilage powder per day.

15. A method of treating a malignant carcinoma of the colo-rectal area which comprises orally administering to a patient afflicted with said colo-rectal carcinoma a solid dosage form containing an effective amount for treating said carcinoma of finely divided cartilage powder having a particle size between about 1 micron and about 500 microns, said cartilage powder being derived from a cartilage bearing animal, fish or reptile, and consisting essentially of defatted and essentially pure granulated cartilage material substantially free from adhering tissue.

16. The method of claim 15 wherein said effective amount comprises between about 3 and 12 grams of said cartilage powder per day.

17. The method of inducing remission of a carcinoma of the prostate gland which comprises administering to a patient afflicted with said prostate carcinoma an effective amount for producing remission of said prostate carcinoma of a solid oral dosage form containing from about 250 to about 500 milligrams of finely divided cartilage powder having a particle size between about 40 and 100 microns, said cartilage powder being derived from a cartilage bearing animal, fish or reptile and consisting essentially of defatted and essentially pure granulated cartilage material, essentially free of adhering tissue.

18. The method of inducing remission of a carcinoma of the ovary which comprises administering to a patient afflicted with said ovarian carcinoma an effective amount for producing remission of said carcinoma of a solid oral dosage form containing from about 250 to about 500 milligrams of finely divided cartilage powder having a particle size between about 40 and about 100 microns, said cartilage powder being derived from a cartilage bearing animal, fish or reptile and consisting essentially of defatted and essentially pure granulated cartilage material, essentially free of adhering tissue.

19. The method of inducing remission of a carcinoma of the breast which comprises administering to a patient afflicted with said breast carcinoma an effective amount for producing remission of said carcinoma of a solid oral dosage form containing from about 250 to about 500 milligrams of finely divided cartilage powder having a particle size between about 40 and about 100 microns, said cartilage powder being derived from a cartilage bearing animal, fish or reptile and consisting essentially of defatted and essentially pure granulated cartilage material, essentially free of adhering tissue.

20. The method of inducing remission of a carcinoma of the colo-rectal area which comprises administering to a patient afflicted with said colo-rectal carcinoma an effective amount for producing remission of said carcinoma of a solid oral dosage form containing from about 250 to about 500 milligrams of finely divided cartilage powder having a particle size between about 40 and about 100 microns, said cartilage powder being derived from a cartilage bearing animal, fish or reptile and consisting essentially of defatted and essentially pure granulated cartilage material, essentially free of adhering tissue.

* * * * *